US010244924B2

(12) United States Patent
Ogawa

(10) Patent No.: US 10,244,924 B2
(45) Date of Patent: Apr. 2, 2019

(54) ENDOSCOPE

(71) Applicant: OLYMPUS CORPORATION, Tokyo (JP)

(72) Inventor: Tomoaki Ogawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 40 days.

(21) Appl. No.: 15/376,983

(22) Filed: Dec. 13, 2016

(65) Prior Publication Data

US 2017/0086654 A1 Mar. 30, 2017

Related U.S. Application Data

(63) Continuation of application No. PCT/JP2015/077609, filed on Sep. 29, 2015.

(30) Foreign Application Priority Data

Mar. 18, 2015 (JP) .................................. 2015-055299

(51) Int. Cl.
*A61B 1/04* (2006.01)
*A61B 1/00* (2006.01)
(Continued)

(52) U.S. Cl.
CPC ........ *A61B 1/00128* (2013.01); *A61B 1/0055* (2013.01); *A61B 1/0056* (2013.01);
(Continued)

(58) Field of Classification Search
CPC ...... A61B 1/00128; A61B 1/018; A61B 1/012
(Continued)

(56) References Cited

U.S. PATENT DOCUMENTS 4,832,003 A * 5/1989 Yabe ...................... A61B 1/051
348/65
5,569,157 A * 10/1996 Nakazawa ........... A61B 1/0008
600/104
(Continued)

FOREIGN PATENT DOCUMENTS

JP H01-152602 U 10/1989
JP H09-253035 A 9/1997
(Continued)

OTHER PUBLICATIONS

International Search Report dated Dec. 15, 2015 issued in PCT/JP2015/077609.
(Continued)

*Primary Examiner* — Matthew J Kasztejna
(74) *Attorney, Agent, or Firm* — Scully, Scott, Murphy & Presser, P.C.

(57) ABSTRACT

An endoscope includes: an insertion section configured to be inserted into a subject; a bending section disposed on a distal end side of the insertion section and bendable in at least one direction; a distal end member connected to a distal end side of the bending section and having a passage to allow a treatment tool to project from the distal end member; a tube inserted into the bending section to allow the treatment tool to be inserted into the tube and having a recessed portion on an inner surface of a distal end side of the tube; and a connection section having a central axis and having one end fixed to the distal end member to be communicated with the passage, and having a projecting portion at the other end of the connection section, projecting along the central axis so as to be fitted into the recessed portion.

20 Claims, 8 Drawing Sheets

(51) Int. Cl.
    *A61B 1/012*     (2006.01)
    *A61B 1/005*     (2006.01)
    *A61B 1/018*     (2006.01)
    *A61B 8/12*     (2006.01)
    *A61B 8/00*     (2006.01)

(52) U.S. Cl.
    CPC .......... *A61B 1/00119* (2013.01); *A61B 1/012* (2013.01); *A61B 1/018* (2013.01); *A61B 8/12* (2013.01); *A61B 8/445* (2013.01); *A61B 8/4483* (2013.01)

(58) Field of Classification Search
    USPC ................. 600/123, 129–130, 141–142, 153
    See application file for complete search history.

(56) References Cited

U.S. PATENT DOCUMENTS

| | | | | |
|---|---|---|---|---|
| 5,685,823 A | * | 11/1997 | Ito | A61B 1/00091 600/121 |
| 5,746,695 A | * | 5/1998 | Yasui | A61B 1/00091 600/121 |
| 5,976,074 A | * | 11/1999 | Moriyama | A61B 1/00078 600/139 |
| 6,582,360 B1 | * | 6/2003 | Torii | A61B 1/018 600/127 |
| 7,828,722 B2 | * | 11/2010 | Ooyatsu | A61B 1/00096 600/109 |
| 8,425,407 B2 | | 4/2013 | Sato et al. | |
| 2004/0077927 A1 | | 4/2004 | Ouchi | |
| 2013/0150667 A1 | | 6/2013 | Mitamura et al. | |

FOREIGN PATENT DOCUMENTS

| | | |
|---|---|---|
| JP | 2000-342516 A | 12/2000 |
| JP | 2002-000545 A | 1/2002 |
| JP | 2010-063795 A | 3/2010 |

OTHER PUBLICATIONS

Extended Supplementary European Search Report dated Nov. 19, 2018 in European Patent Application No. 15 88 5547.8.

* cited by examiner

ENDOSCOPE

CROSS REFERENCES TO RELATED APPLICATIONS

This application is a continuation of PCT international application Ser. No. PCT/JP2015/077609, filed on Sep. 29, 2015 which designates the United States, incorporated herein by reference, and which claims the benefit of priority from Japanese Patent Application No. 2015-055299, filed on Mar. 18, 2015, incorporated herein by reference.

BACKGROUND

1. Technical Field

The disclosure relates to an endoscope.

2. Related Art

Conventionally, an endoscope has been known which is configured such that a soft and elongated insertion section is inserted into a subject such as a human to observe inside the subject (e.g., see JP 9-253035 A).

In an endoscope described in JP 9-253035 A, an insertion section includes a distal end body (hereinafter referred to as distal end member), and a bendable angle portion (hereinafter referred to as bending section) positioned on a proximal end side of the insertion portion relative to the distal end member (on a side separated from a distal end), and fixed to the distal end member. The insertion section includes a treatment tool insertion channel (hereinafter referred to as channel) through which various treatment tools are configured to be inserted.

The channel includes a treatment tool passage disposed in the distal end member, a cylindrical ferrule (hereinafter referred to as connection section) fitted into the treatment tool passage, and a tube disposed in the bending section and connected to the connection section. A treatment tool is inserted through the tube, and protrudes outward from the distal end of the insertion section through the connection section and the treatment tool passage.

However, in the endoscope described in JP 9-253035 A, the following situations may occur.

FIGS. 6A and 6B are diagrams illustrating situations of a channel 100 of the conventional endoscope. Specifically, FIG. 6A is a cross-sectional view of the conventional channel 100 when a connection section 200 is connected to a tube 300. FIG. 6B is a diagram illustrating a state of the connection section 200 and the tube 300 in the conventional channel 100 when the bending section is bent.

Specifically, the connection section 200 has an end portion 210 and the tube 300 has an inner surface, and while the cylindrical connection section 200 is fitted into the tube 300, the end portion 210 and the inner surface of the tube 300 do not form a continuous surface, and a step S appears between the end portion 210 and the inner surface of the tube 300 as illustrated in FIG. 6A.

As illustrated in FIG. 6B, when a treatment tool is used while the bending section is bent (bent upward in FIG. 6B), the treatment tool moves while making contact with the lower side of the inner surface of the tube 300 in FIG. 6B, and thus makes contact with the step S.

That is, unfortunately, the treatment tool is caught by the step S and causes abrasion of the inner surface of the tube 300, or the treatment tool makes contact with the step S and deterioration of the treatment tool occurs.

Therefore, there is a need to provide an endoscope which can reduce abrasion of an inner surface of a tube or deterioration of a treatment tool.

SUMMARY

In some embodiments, an endoscope includes: an insertion section configured to be inserted into a subject; a bending section disposed on a distal end side of the insertion section and bendable in at least one direction; a distal end member connected to a distal end side of the bending section and having a treatment tool passage to allow a treatment tool to project outward from the distal end member; a tube inserted into the bending section to allow the treatment tool to be inserted into the tube and having a recessed portion on an inner surface of a distal end side of the tube; and a connection section having a central axis and having one end fixed to the distal end member so as to be communicated with the treatment tool passage, the connection section having a projecting portion at the other end of the connection section, the projecting portion projecting along the central axis so as to be fitted into the recessed portion of the tube.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiment(s)") will be described below with reference to the drawings. The present invention is not limited to the embodiments described below. The same reference signs are used to designate the same elements throughout the drawings.

Outline of Configuration of Endoscope System

Figure 1:
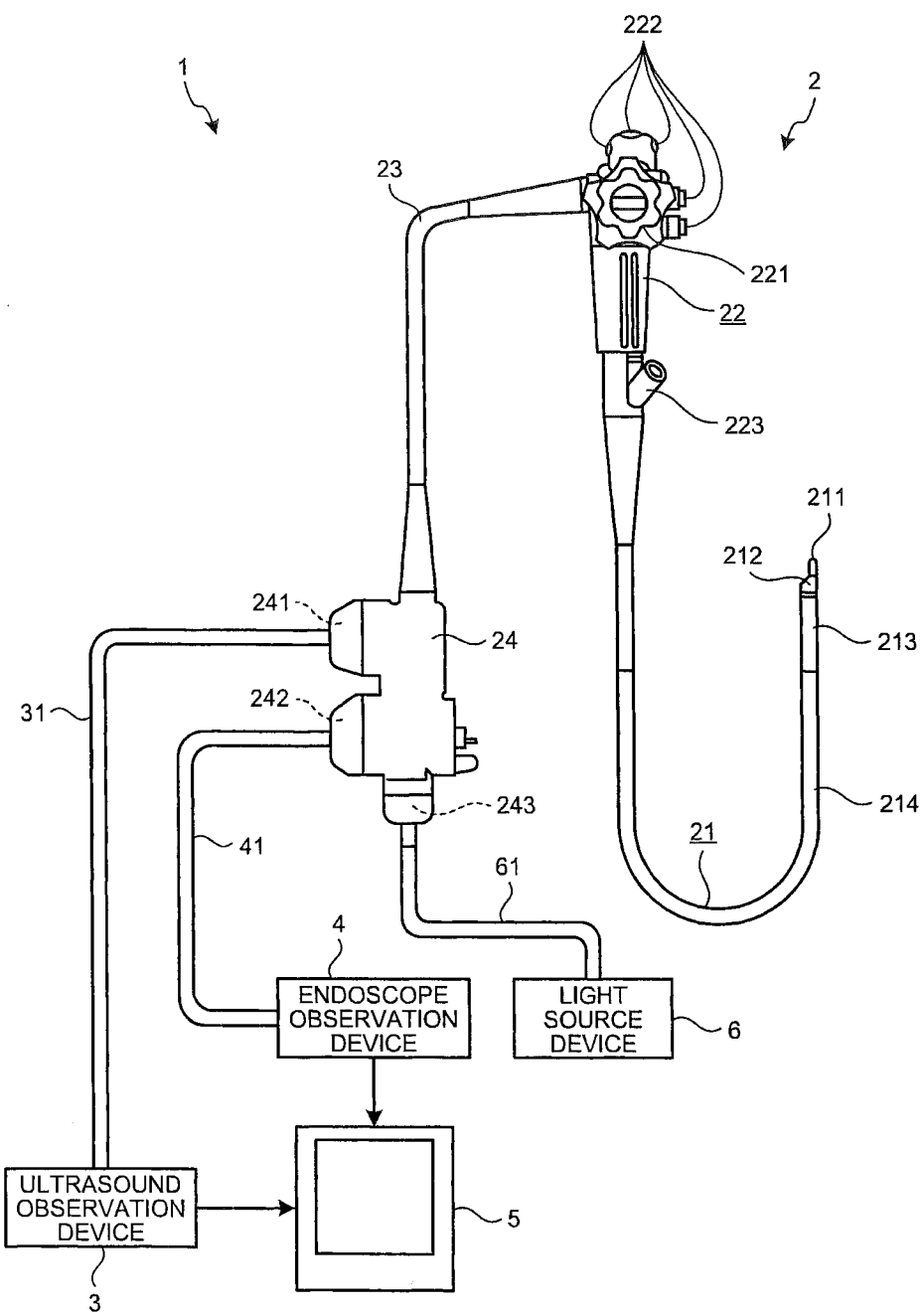
FIG. 1 is a schematic view of an endoscope system according to an embodiment of the present invention.

FIG. 1 is a schematic view of an endoscope system 1 according to an embodiment of the present invention.

The endoscope system 1 is a system performing ultrasonic diagnosis in a subject such as a human, using an ultrasound endoscope. As illustrated in FIG. 1, the endoscope system 1 includes an endoscope 2, an ultrasound observation device 3, an endoscope observation device 4, a display device 5, and a light source device 6.

The endoscope 2 is an ultrasound endoscope configured to be partially inserted into the subject, and having a function of transmitting ultrasound pulses toward a body wall in the subject, receiving an ultrasound echo reflected from the subject, and outputting an echo signal, and a function of imaging inside the subject and outputting an image signal.

A detailed configuration of the endoscope 2 will be described later.

The ultrasound observation device 3 is electrically connected to the endoscope 2 through an ultrasound cable 31 (FIG. 1), and outputs a pulse signal to the endoscope 2 and receives an echo signal input from the endoscope 2, through the ultrasound cable 31. Then, the ultrasound observation device 3 performs predetermined processing on the echo signal to generate an ultrasound image.

The endoscope observation device 4 is electrically connected to the endoscope 2 through a video cable 41 (FIG. 1), and receives an image signal input from the endoscope 2 through the video cable 41. Then, the endoscope observation device 4 performs predetermined processing on the image signal to generate an endoscopic image.

The display device 5 is configured using liquid crystal or organic electro luminescence (EL), and displays the ultrasound image generated in the ultrasound observation device 3, the endoscopic image generated in the endoscope observation device 4, or the like.

The light source device 6 is connected to the endoscope 2 through an optical fiber cable 61 (FIG. 1), and supplies illumination light illuminating inside the subject, to the endoscope 2, through the optical fiber cable 61.

Configuration of Endoscope

As illustrated in FIG. 1, the endoscope 2 includes an insertion section 21, an operating unit 22, a universal cable 23, and a connector 24.

Note that, "distal end" described below represents an end portion positioned on a distal end side of the insertion section 21. In addition, "proximal end" described below represents an end portion positioned on a side away from the distal end of the insertion section 21 (on the side of the operating unit 22).

The insertion section 21 is a portion inserted into the subject. As illustrated in FIG. 1, the insertion section 21 includes an ultrasound probe 211 provided on the distal end side, a hard member 212 connected to the proximal end side of the ultrasound probe 211, a bending section 213 connected on the proximal end side of the hard member 212 to be bendable, and a flexible tube section 214 connected to the proximal end side of the bending section 213.

The insertion section 21 has therein a light guide (not illustrated) for transmitting illumination light supplied from the light source device 6, an image guide (not illustrated) for guiding an optical image inside the subject, a plurality of signal cables for transmitting various signals (e.g., a signal cable 25 (see FIG. 2) electrically connected to the ultrasound cable 31 through the universal cable 23), and a tube 27 (see FIG. 2) through which various treatment tools (e.g., puncture needle 26 (see FIG. 2)) are configured to be inserted.

A detailed configuration of the distal end side of the insertion section 21 will be described later.

The operating unit 22 is a portion connected to the proximal end side of the insertion section 21, and receives various operation from a physician or the like. As illustrated in FIG. 1, the operating unit 22 includes a bending knob 221 for bendably operating the bending section 213, and a plurality of operation members 222 for performing various operations.

Further, in the operating unit 22, a treatment tool insertion opening 223 is formed which communicates with the tube 27 disposed in the insertion section 21 to insert various treatment tools (e.g., to insert the puncture needle 26 (see FIG. 2)) through the tube 27.

Still further, in the operating unit 22, an imaging sensor (not illustrated) and an optical system (not illustrated) are disposed. The imaging sensor outputs an image signal according to the optical image in the subject, and the optical system (not illustrated) forms the optical image transmitted by the image guide, on the imaging sensor.

The universal cable 23 is a cable having one end connected to the operating unit 22, and the signal cables for transmitting various signals, an optical fiber for transmitting illumination light supplied from the light source device 6, and the like are disposed therein.

The connector 24 is provided at the other end of the universal cable 23. The connector 24 includes first to third connector portions 241 to 243 to which the ultrasound cable 31, the video cable 41, and the optical fiber cable 61 are respectively connected.

Configuration of Insertion Section

Figure 2:
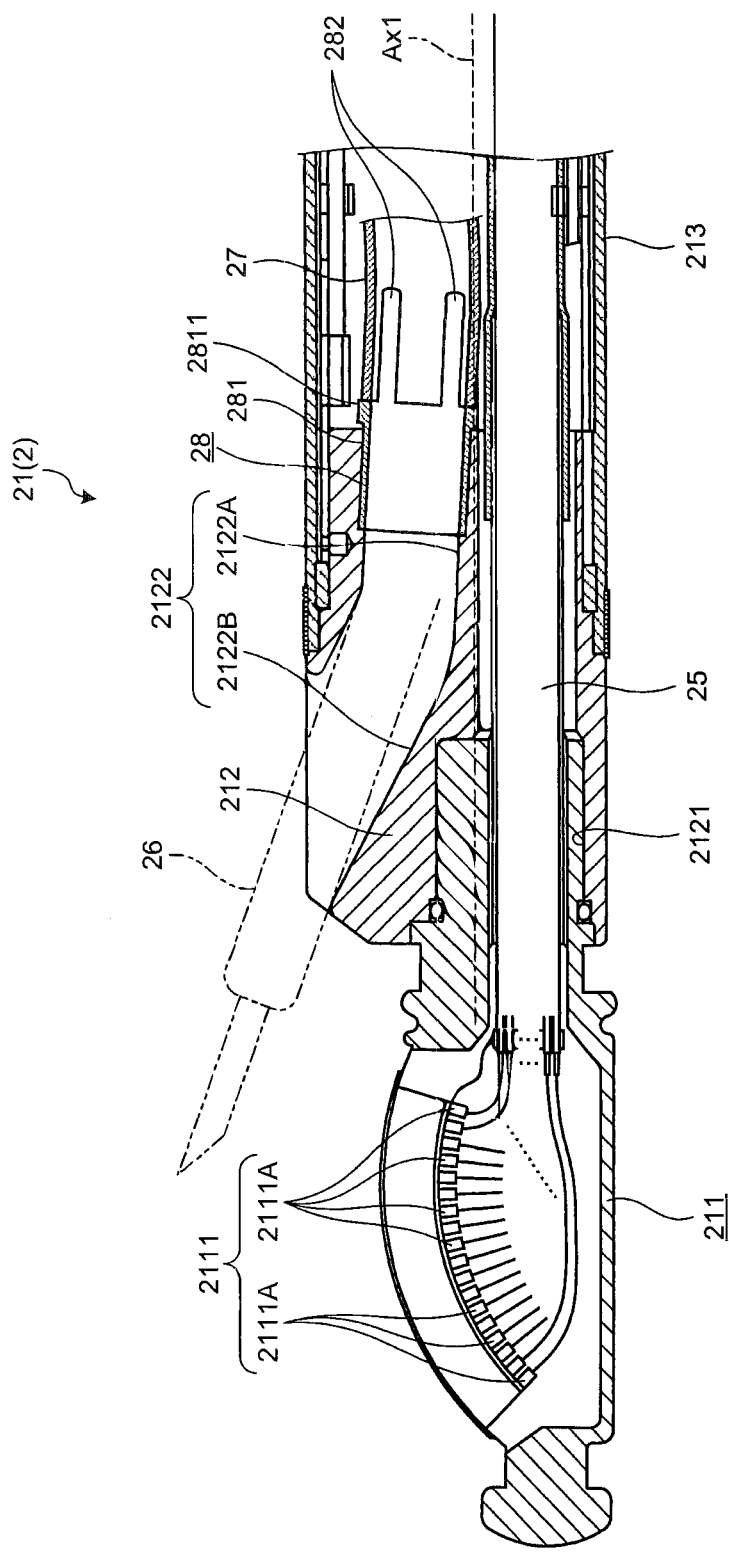
FIG. 2 is an enlarged cross-sectional view of a distal end side of an insertion section of FIG. 1.

FIG. 2 is an enlarged cross-sectional view of the distal end side of the insertion section 21. Specifically, FIG. 2 is a cross-sectional view of the distal end side of the insertion section 21, which is taken along a cut plane extending along an axial direction of the insertion section 21.

Configurations of the ultrasound probe 211, the hard member 212, and the bending section 213 will be described below.

As illustrated in FIG. 2, the ultrasound probe 211 is a convex ultrasound probe, and has a transducer unit 2111 in which multiple ultrasound transducers 2111A are regularly disposed to form a convex arcuate shape.

Here, The ultrasound transducer 2111A has an acoustic lens, a piezoelectric element, and a matching layer, and obtains an ultrasound echo contributing to an ultrasound tomographic image captured inside the body wall in the subject.

The transducer unit 2111 electrically converts the pulse signal input from the ultrasound observation device 3 through a signal cable 25, to ultrasound pulses, and transmits the ultrasound pulses into the subject. Further, the transducer unit 2111 converts the ultrasound echo reflected from the subject to an electrical echo signal, and outputs the echo signal to the ultrasound observation device 3 through the signal cable 25.

The bending section 213 is a portion having a cylindrical shape, and bent according to operation of the bending knob 221 by the physician or the like.

Note that, specific illustration is omitted, but in the bending section 213, four angle wires are inserted, in addition to the light guide, the image guide, the plurality of signal cables (e.g., signal cable 25), and the tube 27. The four angle wires each have one end connected to the bending knob 221, and the other end connected on the distal end side of the bending section 213. When the physician or the like operates the bending knob 221, the four angle wires are appropriately pulled and released, and the bending section 213 is bent in an upward direction (first direction D1 (see FIG. 3B)) or a downward direction (second direction D2 (see FIG. 3B)), in FIG. 2, and in a direction perpendicular to the drawing (third and fourth directions D3 and D4 (see FIG. 3B) perpendicular to the first and second directions D1 and D2), in FIG. 2.

The hard member 212 has a function as a distal end member according to the present invention, is a hard member made of a resin material, and has a substantially columnar shape.

In the hard member 212, a mounting hole 2121, a treatment tool passage 2122, an imaging hole (not illustrated), and an illumination hole (not illustrated) are formed, as illustrated in FIG. 2.

The imaging hole is a hole used to obtain an optical image in the subject, and penetrates the hard member 212 from the proximal end to a distal end. In the imaging hole, an input end side of the image guide is inserted. Further, to the input end of the image guide, an objective lens (not illustrated) is connected.

The illumination hole is a hole used to illuminate inside the subject with illumination light, and penetrates the hard member 212 from the proximal end to the distal end. In the illumination hole, an output end side of the light guide is inserted.

The mounting hole 2121 is a hole used to mount the ultrasound probe 211, and penetrates the hard member 212 from the proximal end to the distal end. As illustrated in FIG. 2, in the mounting hole 2121, the ultrasound probe 211 is mounted on a distal end side, and the signal cable 25 electrically connected to the transducer unit 2111 is inserted.

The treatment tool passage 2122 is a hole for projecting various treatment tools (e.g., puncture needle 26 (FIG. 2)) outward, and the hole has a circular cross-section penetrating upward, from the proximal end to the distal end of the hard member 212, in FIG. 2.

More specifically, as illustrated in FIG. 2, the treatment tool passage 2122 includes a proximal end side hole 2122A and a distal end side hole 2122B.

The proximal end side hole 2122A is formed to be inclined slightly upward, at a first inclination angle relative to a central axis Ax1 (FIG. 2) of the hard member 212, from the proximal end to the distal end of the hard member 212, in FIG. 2.

The distal end side hole 2122B communicates with the proximal end side hole 2122A, and is formed to be inclined upward, at a second inclination angle larger than the first inclination angle, relative to the central axis Ax1 of the hard member 212, at the distal end of the hard member 212, in FIG. 2.

As illustrated in FIG. 2, a connection section 28 is fixed in the treatment tool passage 2122 (proximal end side hole 2122A).

Configurations of Connection Section and Tube

Configurations of the connection section 28 and the tube 27 will described below.

Figure 3A:
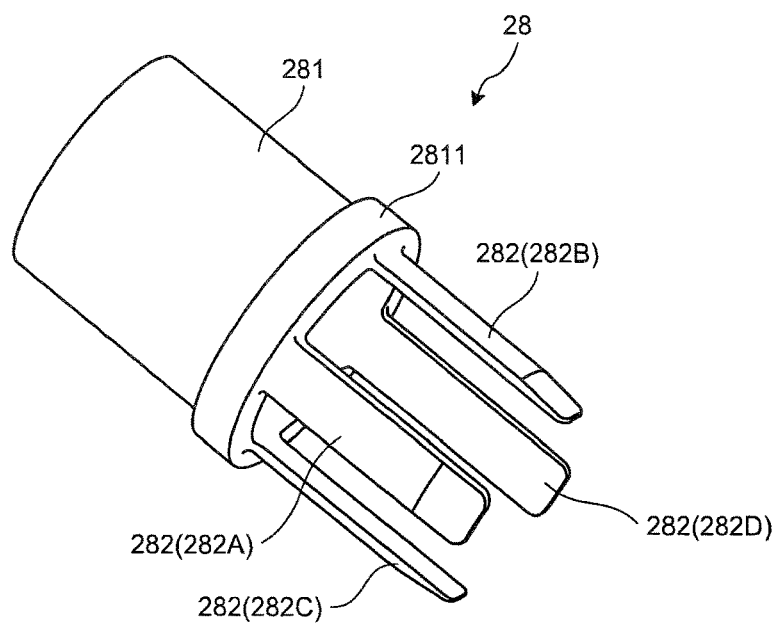
FIG. 3A is a diagram illustrating a configuration of a connection section of FIG. 2.
Figure 3B:
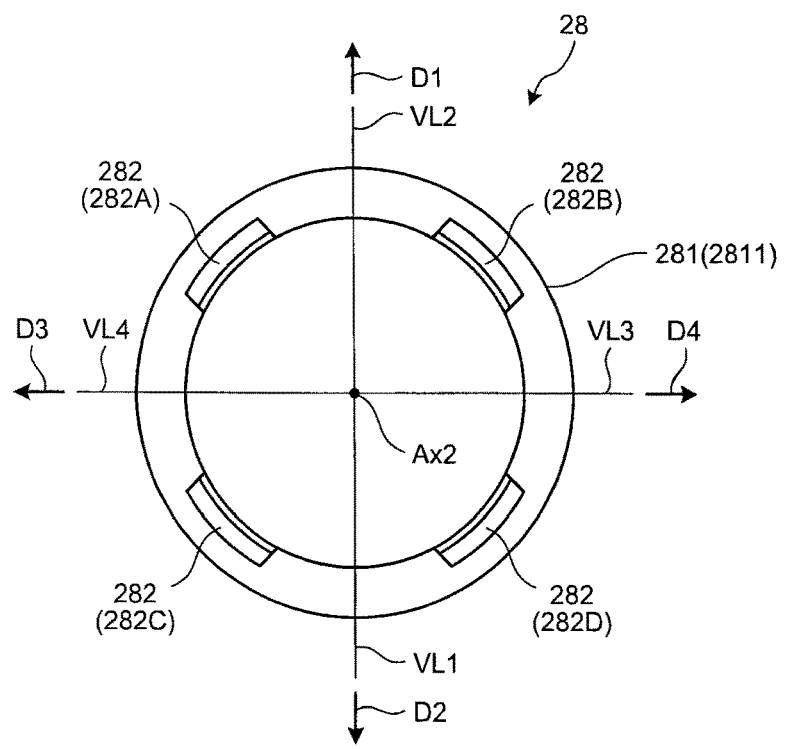
FIG. 3B is a diagram illustrating a configuration of the connection section of FIG. 2.

FIGS. 3A and 3B are diagrams illustrating a configuration of the connection section 28. Specifically, FIG. 3A is a perspective view of the connection section 28, viewed from the proximal end side. FIG. 3B is a diagram of the connection section 28, viewed from the proximal end side along a central axis Ax2 of the connection section 28. A vertical direction in FIG. 3B and a vertical direction in FIG. 2 are oriented in the same direction.

The connection section 28 is made of a metal material, and has a cylindrical shape as illustrated in FIG. 3A or FIG. 3B. The connection section 28 is connected to the treatment tool passage 2122 and the tube 27 to cause the treatment tool passage 2122 and the tube 27 to communicate with each other (FIG. 2).

As illustrated in FIG. 3A or FIG. 3B, the connection section 28 includes a connection section body 281 and a projecting portion 282.

The connection section body 281 is a portion having a cylindrical shape, and fitted to the treatment tool passage 2122 (proximal end side hole 2122A).

The connection section body 281 has a proximal end, and the proximal end has an outer peripheral surface on which a protruding portion 2811 having an outer diameter dimension larger than that of the other portion is formed, as illustrated in FIG. 3A or 3B.

The projecting portion 282 projects along a central axis Ax2 from an end portion of proximal end side of the connection section body 281, and fitted into the tube 27.

More specifically, the projecting portion 282 includes an arcuate structure extending about the central axis Ax2, as illustrated in FIG. 3B. The projecting portion 282 has a surface facing the central axis Ax2, and the surface is formed at the end portion of proximal end side of the connection section body 281 to extend to an inner surface of the connection section body 281. Further, the projecting portion 282 has a thickness dimension (dimension along radial direction of the connection section 28) which is set smaller than a thickness dimension of the proximal end (including the protruding portion 2811) of the connection section body 281. Still further, the projecting portion 282 has an end portion of proximal end side which has a tapered shape gradually reduced in thickness dimension toward the proximal end side.

In the embodiment, there are provided four projecting portions 282, as illustrated in FIG. 3A or 3B. Hereinafter, the four projecting portions 282 are defined as first to fourth projecting portions 282A to 282D. All of the first to fourth projecting portions 282A to 282D have the same shape.

The first to fourth projecting portions 282A to 282D are provided at positions as described below.

Here, a virtual line extending from the central axis Ax2 in a direction (second direction D2) opposite to the first direction D1 being a bending direction of the bending section 213, when viewed from a direction parallel to the central axis Ax2, is defined as a first virtual line VL1 (FIG. 3B). Further, a virtual line extending from the central axis Ax2 in a direction (first direction D1) opposite to the second direction D2 being the bending direction of the bending section 213 is defined as a second virtual line VL2 (FIG. 3B). Still further, a virtual line extending from the central axis Ax2 in a direction (fourth direction D4) opposite to the third direction D3 being the bending direction of the bending section 213 is defined as a third virtual line VL3 (FIG. 3B). Still another further, a virtual line extending from the central axis Ax2 in a direction (third direction D3) opposite to the fourth direction D4 being the bending direction of the bending section 213 is defined as a fourth virtual line VL4 (FIG. 3B).

When the first to fourth virtual lines VL1 to VL4 are located as described above, the first to fourth projecting portions 282A to 282D are deviated from the first to fourth virtual lines VL1 to VL4, viewed in the direction parallel to the central axis Ax2, as illustrated in FIG. 3B. The first to fourth projecting portions 282A to 282D are provided at positions 90° rotationally symmetric about the central axis Ax2.

Figure 4A:
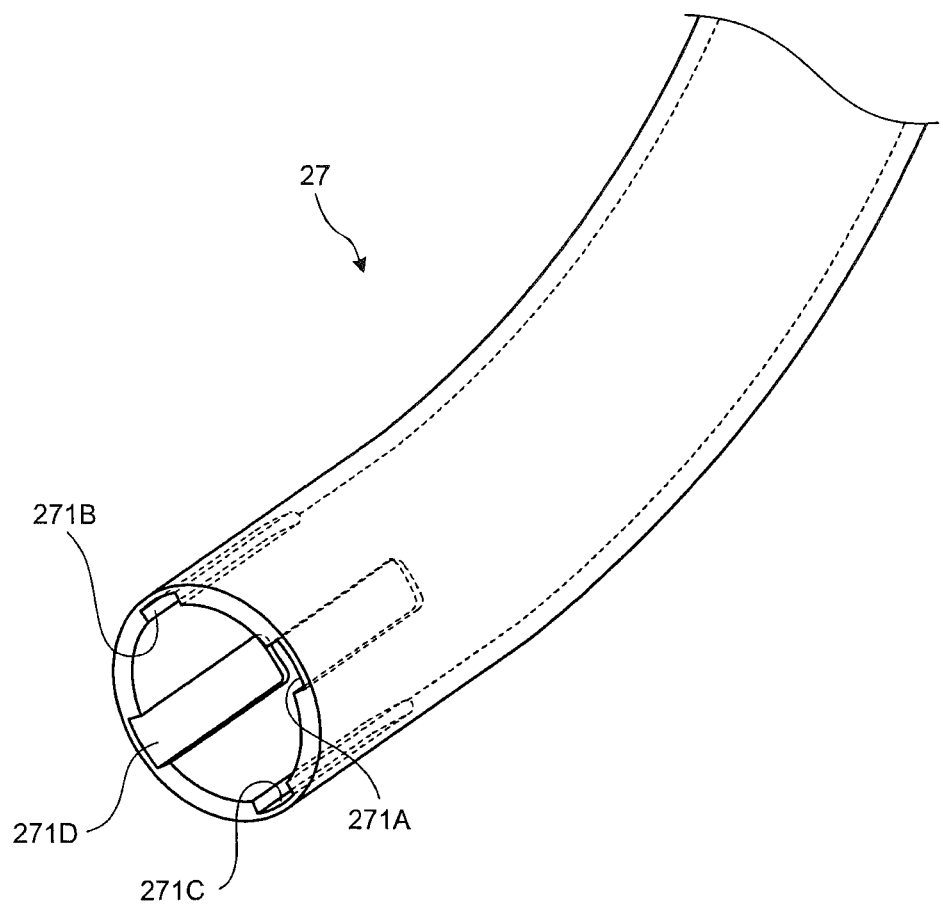
FIG. 4A is a diagram illustrating a configuration of a tube of FIG. 2.
Figure 4B:
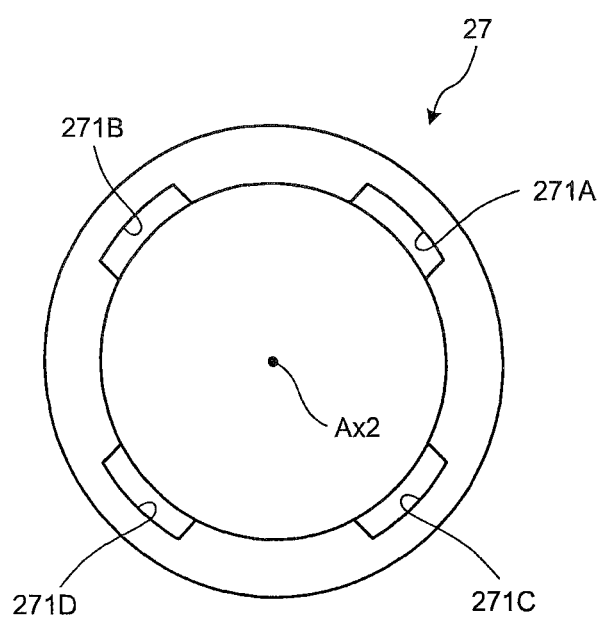
FIG. 4B is a diagram illustrating a configuration of the tube of FIG. 2.

FIGS. 4A and 4B are diagrams illustrating a configuration of the tube 27. Specifically, FIG. 4A is a perspective view of the tube 27 which is viewed from a distal end side. FIG. 4B is a diagram of the tube 27 which is viewed from a distal end side along the central axis Ax2. A vertical direction in FIG. 4B and a vertical direction in FIG. 3B are oriented in the same direction.

The tube 27 is a flexible cylindrical tube. The tube 27 has an inner diameter dimension set substantially the same as an inner diameter dimension of the connection section 28. The tube 27 has an end portion of proximal end side connected to the treatment tool insertion opening 223. Further, the tube 27 has an end portion of distal end side into which the first to fourth projecting portions 282A to 282D are fitted and fastened with an adhesive or the like, and the tube 27 is connected to the connection section 28. Then, the connection section 28 (connection section body 281) is fitted to the treatment tool passage 2122 (proximal end side hole 2122A) to cause the treatment tool insertion opening 223 and the treatment tool passage 2122 to communicate with each other through the tube 27 and the connection section 28. The treatment tool insertion opening 223 and the treatment tool passage 2122 are communicated with each other as described above, so that various treatment tools (e.g., puncture needle 26) inserted through the treatment tool insertion opening 223 are allowed to project outward from the distal end of the insertion section 21, through the tube 27, the connection section 28, and the treatment tool passage 2122 (FIG. 2).

The tube 27 has an inner surface on which first to fourth recessed portions 271A to 271D are formed at positions corresponding to the first to fourth projecting portions 282A to 282D. The first to fourth recessed portions 271A to 271D extend from the distal end toward the proximal end to allow the first to fourth projecting portions 282A to 282D to be inserted therein, respectively, as illustrated in FIG. 4A or 4B. All of the first to fourth recessed portions 271A to 271D have the same shape.

More specifically, the first recessed portion 271A has a depth dimension (dimension along radial direction of the tube 27) which is set substantially the same as a thickness dimension of the first projecting portion 282A. Further, the first recessed portion 271A has a width dimension (dimension along circumferential direction of the tube 27) which is set substantially the same as a width dimension of the first projecting portion 282A (dimension along circumferential direction of the connection section 28). Still further, the first recessed portion 271A has a length dimension (dimension along the central axis Ax2) which is set substantially the same as a length dimension of the first projecting portion 282A (dimension along the central axis Ax2). The second to fourth recessed portions 271B to 271D are configured in a similar manner.

Therefore, while the first to fourth projecting portions 282A to 282D are inserted into the first to fourth recessed portions 271A to 271D (the first to fourth projecting portions 282A to 282D are fitted into the tube 27), the distal end of the tube 27 abuts on the proximal end (protruding portion 2811) of the connection section body 281. Further, in this state, a pressing force acting on the inner surface of the tube 27 from the first to fourth projecting portions 282A to 282D is reduced, and deformation of the distal end side of the tube 27 is inhibited. That is, in the abutment state, the inner surface of the connection section body 281 and the inner surface of the tube 27 are connected into a continuous surface.

Figure 5:
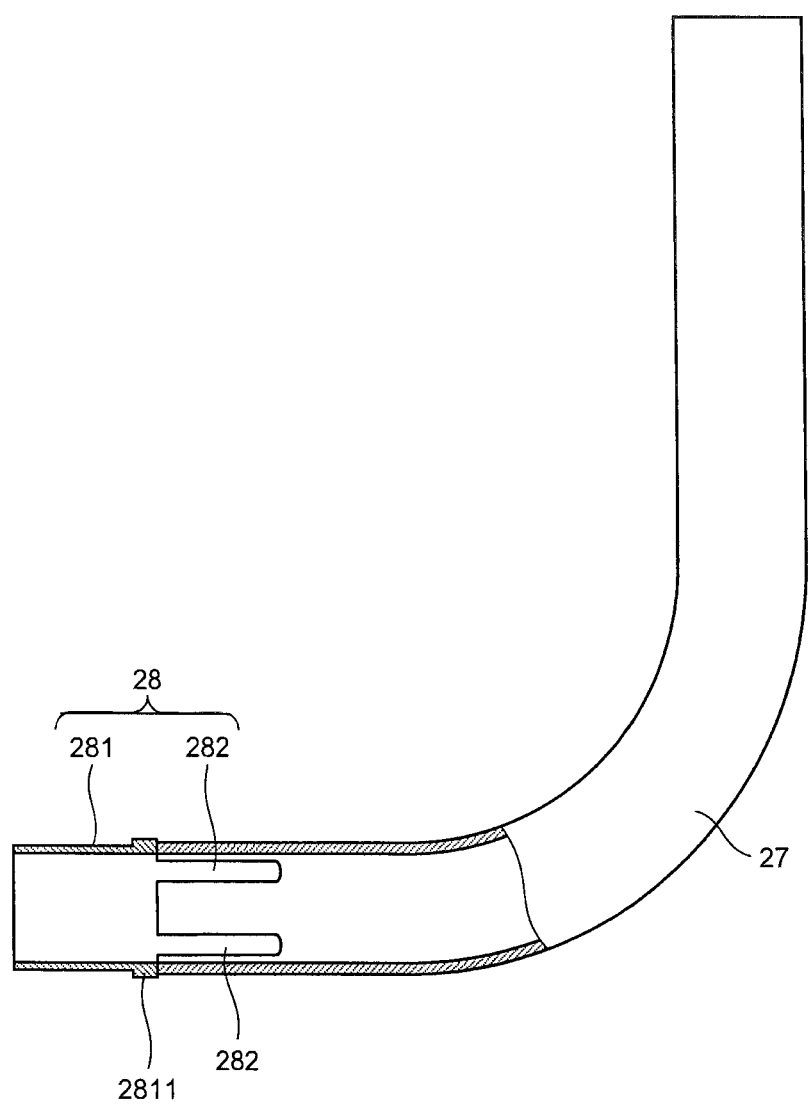
FIG. 5 is a diagram illustrating the effect of an embodiment of the present invention.

FIG. 5 is a diagram illustrating the effect of an embodiment of the present invention. Specifically, FIG. 5 is a partial cross-sectional view (taken along cut plane extending along central axis Ax2) illustrating a state of the tube 27 and the connection section 28 while the bending section 213 is bent in the first direction D1.

Figure 6A:
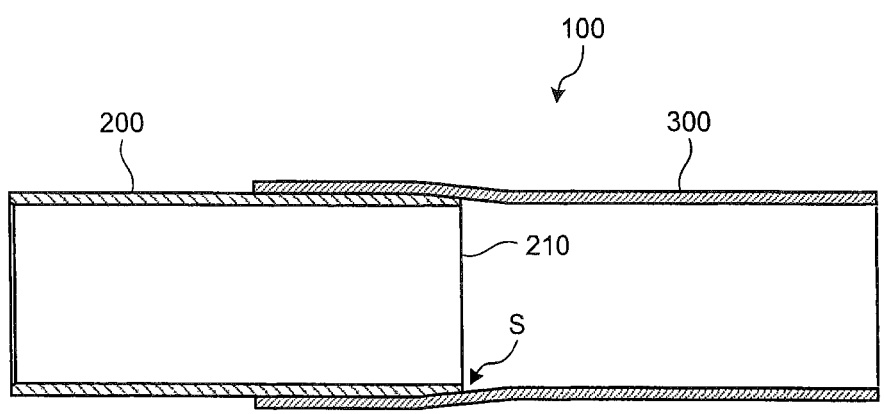
FIG. 6A is a diagram illustrating a situation of a channel in a conventional endoscope.
Figure 6B:
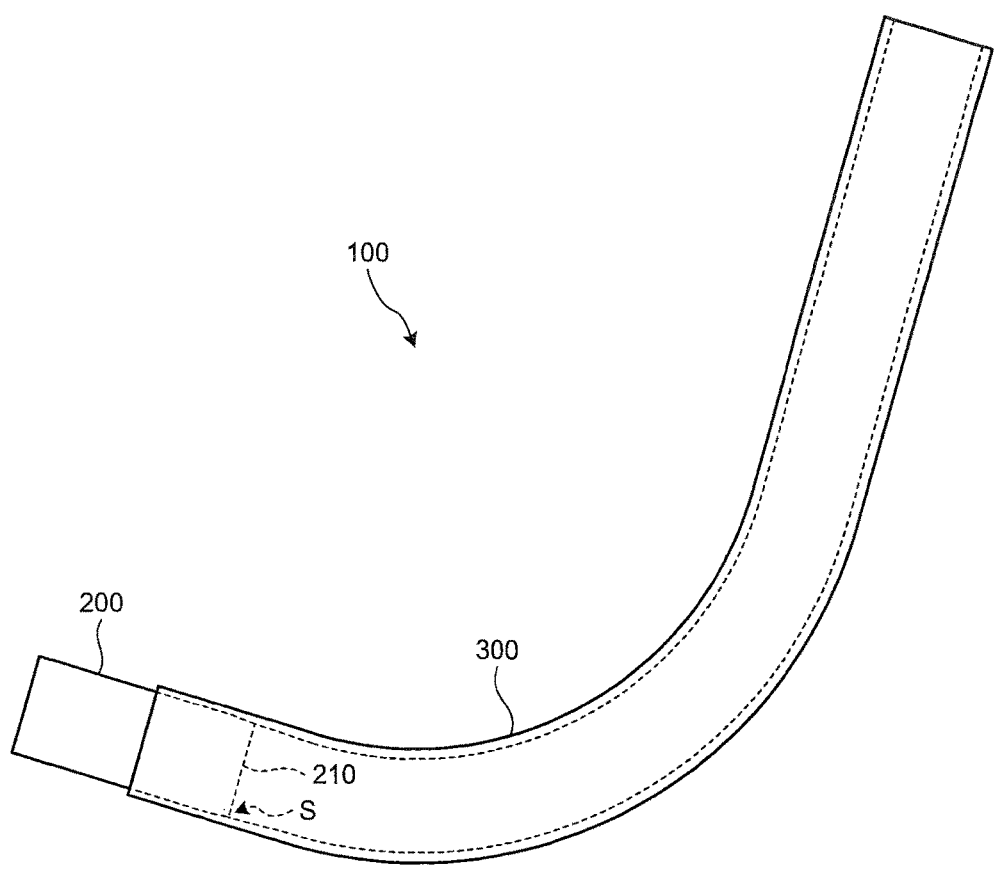
FIG. 6B is a diagram illustrating the situation of the channel in the conventional endoscope.

As described above, in the endoscope 2 according to the embodiment, the connection section 28 is provided with the first to fourth projecting portions 282A to 282D fitted into the tube 27. The first to fourth projecting portions 282A to 282D are deviated from the first to fourth virtual lines VL1 to VL4, when viewed from the direction parallel to the central axis Ax2. That is, as illustrated in FIG. 5, the first to fourth projecting portions 282A to 282D are fitted into the tube 27 to connect the connection section 28 with the tube 27 such that a proximal end portion (projecting portion 282) of the connection section 28 is not located where the step S (FIGS. 6A and 6B) has appeared in the conventional technique which causes the treatment tool to contact with the step upon bending the bending section.

Thus, according to the endoscope 2 of the embodiment, even when the treatment tool is used while bending the bending section 213 in any of the first to fourth directions D1 to D4, the treatment tool is not caught at a connected portion between the connection section 28 and the tube 27, thereby effectively reducing abrasion of the inner surface of the tube 27 or deterioration of the treatment tool.

Further, in the endoscope 2 according to the embodiment, the first to fourth recessed portions 271A to 271D are formed at positions corresponding to the first to fourth projecting portions 282A to 282D, on the inner surface of the tube 27. Therefore, the first to fourth projecting portions 282A to 282D are prevented from pressing the inner surface of the tube 27 to inhibit deterioration on the distal end side of the tube 27, and, as illustrated in FIG. 5, the inner surface of the connection section body 281 and the inner surface of the tube 27 are formed into a continuous surface. Accordingly, the step is prevented from being generated between the end portion of proximal end side of the connection section body 281 and the inner surface of the tube 27, and the treatment tool can be also prevented from being caught at the position.

Further, in the endoscope 2 according to the embodiment, the projecting portion 282 has a tapered shape. Therefore, when the connection section 28 and the tube 27 are connected, the projecting portion 282 is readily inserted into the tube 27.

Other Embodiments

Although the embodiment for carrying out the present invention has been described above, the present invention is not limited only to the above-mentioned embodiment.

In the embodiment described above, the bending section 213 is bendable in four directions, that is, the first to fourth directions D1 to D4, but another configuration may be employed as long as the bending section 213 is bendable in at least one direction.

For example, if the bending section 213 is bendable only in the first direction D1, the projecting portion 282 may be deviated from the first virtual line VL1 only, and the first to fourth projecting portions 282A to 282D may be integrated with one another so as to be continuous clockwise from the third projecting portion 282C to fourth projecting portion 282D, in FIG. 3B.

Alternatively, for example, if the bending section 213 is bendable only in two directions, that is, the first and second directions D1 and D2, the projecting portions 282 may be deviated from the first and second virtual lines VL1 and VL2 only, and the first and third projecting portions 282A and 282C may be integrated so as to be continuous clockwise from the third projecting portion 282C to the first projecting portion 282A in FIG. 3B, and the second and fourth projecting portions 282B and 282D may be integrated so as to be continuous from the second projecting portion 282B to the fourth projecting portion 282D.

Thus, the number of projecting portions 282 is also not limited to four, and at least one projecting portion 282 may be provided. The number of the first to fourth recessed portions 271A to 271D is determined accordingly.

In the embodiment described above, the inner surface of the tube 27 is provided with the first to fourth recessed portions 271A to 271D, and the projecting portion 282 has the tapered shape, but tube 27 and the projecting portion 282 are not limited to these configurations, and the object of the present invention can be also achieved by a configuration in which the inner surface of the tube 27 is not provided with the first to fourth recessed portions 271A to 271D, or a configuration in which the projecting portion 282 does not have the tapered shape.

In the embodiment described above, the hard member 212 and the connection section 28 are separately configured, but the hard member 212 and the connection section 28 are not limited to this configuration, and may be integrally formed of the same material.

In the embodiment described above, the endoscope system 1 has both of the function of generating the ultrasound image, and the function of generating the endoscopic image, but the endoscope system 1 is not limited to this configuration, and may be configured to have only one of the functions.

In the embodiment described above, the endoscope system 1 is not limited to medical field use, and the endoscope system 1 may be used in an industrial field, to be used as an endoscope system for observing inside a subject such as a machine structure.

An endoscope according to some embodiments has a connection section having a projecting portion fitted into a tube. The projecting portion is deviated from a virtual line extending from a central axis of the connection section in a direction opposite to a first direction as a bending direction of a bending section when viewed from a direction parallel to the central axis of the connection section. That is, the projecting portion is fitted into the tube to connect the connection section with the tube such that an end portion (projecting portion) of the connection section is not located where a step has appeared in the conventional technique which causes a treatment tool to contact with the step upon bending the bending section.

Thus, according to the endoscope of some embodiments, even when a treatment tool is used while bending the bending section, the treatment tool is not caught at a connected portion between the connection section and the tube, thereby effectively reducing abrasion of an inner surface of the tube or deterioration of the treatment tool.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
  an insertion section configured to be inserted into a subject;
  a bending section disposed on a distal end side of the insertion section and bendable in at least one bending direction;
  a distal end member connected to a distal end side of the bending section and having a treatment tool passage to allow a treatment tool to project outward from the distal end member;
  a tube inserted into the bending section to allow the treatment tool to be inserted into the tube, the tube having at least two trench portions on an inner surface of a distal end side of the tube; and
  a connection section having a central axis and having one end fixed to the distal end member so as to be communicated with the treatment tool passage, the connection section having at least two projecting portions, each having an elongated shape, at the other end of the connection section, the at least two projecting portions projecting along the central axis so as to be respectively fitted into the at least two trench portions of the tube.

2. The endoscope according to claim 1, wherein the at least two projecting portions and respective at least two trench portions, when fitted together, are offset in a circumferential direction around the central axis with respect to the at least one bending direction of the bending section such that the at least two projecting portions and respective at least two trench portions, when fitted together, do not coincide with the bending direction.

3. The endoscope according to claim 1, wherein the each of the at least two projecting portions have a tapered shape.

4. The endoscope according to claim 1, wherein the at least two projecting portions comprise four projecting portions and the at least two trench portions comprise four trench portions.

5. The endoscope according to claim 4, wherein the four projecting portions have the same shape.

6. The endoscope according to claim 5, wherein the four trench portions have the same shape.

7. The endoscope according to claim 1, wherein an inner diameter of the tube is the same as an inner diameter of the connection portion.

8. The endoscope according to claim 1, wherein each of the at least two trench portions of the tube has a depth in a radial direction of the tube, the depth allowing the at least two projection portions to be housed in a respective one of the at least two trench portions such that an inner surface of each of the at least two projection portions is flush with the inner surface of the distal end side of the tube in the radial direction.

9. The endoscope according to claim 1, wherein each of the at least two projecting portions of the tube has a length in a longitudinal direction of the tube, the length allowing the at least two projecting portions to be housed in a respective one of the at least two trench portions such that no gap is formed between a distal end of each of the at least two projecting portions and a proximal end of a respective one of the at least two trench portions in the longitudinal direction.

10. The endoscope according to claim 1, wherein the connection portion has an outward bulging portion with which a distal end of the tube is to be in contact.

11. An endoscope comprising:
  an insertion section configured to be inserted into a subject;
  a bending section disposed on a distal end side of the insertion section and bendable in at least one bending direction;
  a distal end member disposed on a distal end side of the bending section and provided with an opening that allows a treatment tool to project outward therefrom;
  a tube inserted into the bending section to allow the treatment tool to be inserted into the tube, the tube having at least two trench portions on an inner surface of a distal end side of the tube; and a connector having a central axis and at least two projecting portions of elongated shape on one end of the connector, the at least two projecting portions projecting along the central axis, the connector connecting the distal end member and the tube so that the other end of the connector is fixed to the distal end member and the at least two projecting portions are respectively fitted into the at least two trench portions of the tube, thereby to allow the treatment tool inserted into the tube to project from the opening of the distal end member.

12. The endoscope according to claim 11, wherein the at least two projecting portions and respective at least two trench portions, when fitted together, are offset in a circumferential direction around the central axis with respect to the at least one bending direction of the bending section such that the at least two projecting portions and respective at least two trench portions, when fitted together, do not to coincide with the bending direction.

13. The endoscope according to claim 11, wherein each of the at least two projecting portions have a tapered shape.

14. The endoscope according to claim 11, wherein the at least two projecting portions comprise four projecting portions and the at least two trench portions comprise four trench portions.

15. The endoscope according to claim 14, wherein each of the four projecting portions have the same shape.

16. The endoscope according to claim 15, wherein each of the four trench portions have the same shape.

17. The endoscope according to claim 11, wherein an inner diameter of the tube is the same as an inner diameter of the connection portion.

18. The endoscope according to claim 11, wherein each of the at least two trench portions of the tube has a depth in a radial direction of the tube, the depth allowing the at least two projection portions to be housed in a respective one of the at least two trench portions such that an inner surface of each of the at least two projection portions is flush with the inner surface of the distal end side of the tube in the radial direction.

19. The endoscope according to claim 11, wherein each of the at least two projecting portions of the tube has a length in a longitudinal direction of the tube, the length allowing the at least two projecting portions to be housed in a respective one of the at least two trench portions such that no gap is formed between a distal end of each of the at least two projecting portions and a proximal end of a respective one of the at least two trench portions in the longitudinal direction.

20. An insertion section for use with an endoscope, the insertion section being configured to be inserted into a subject, the insertion section comprising:
a bending section disposed on a distal end side of the insertion section and bendable in at least one bending direction;
a distal end member connected to a distal end side of the bending section and having a treatment tool passage to allow a treatment tool to project outward from the distal end member;
a tube inserted into the bending section to allow the treatment tool to be inserted into the tube, the tube having at least two trench portions on an inner surface of a distal end side of the tube; and
a connection section having a central axis and having one end fixed to the distal end member so as to be communicated with the treatment tool passage, the connection section having at least two projecting portions, each having an elongated shape, at the other end of the connection section, the at least two projecting portions projecting along the central axis so as to be respectively fitted into the at least two trench portions of the tube.

* * * * *